United States Patent
Hu et al.

(10) Patent No.: US 10,285,252 B2
(45) Date of Patent: May 7, 2019

(54) DUAL-ENERGY RAY SCANNING SYSTEM, SCANNING METHOD AND INSPECTING SYSTEM

(71) Applicant: Nuctech Company Limited, Beijing (CN)

(72) Inventors: Yu Hu, Beijing (CN); Shangmin Sun, Beijing (CN); Juan Zheng, Beijing (CN); Bicheng Liu, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 241 days.

(21) Appl. No.: 15/278,043

(22) Filed: Sep. 28, 2016

(65) Prior Publication Data
US 2017/0094762 A1    Mar. 30, 2017

(30) Foreign Application Priority Data
Sep. 28, 2015   (CN) .......................... 2015 1 0627055

(51) Int. Cl.
| G21K 1/04 | (2006.01) |
| H05G 1/30 | (2006.01) |
| G01V 5/00 | (2006.01) |
| G01N 23/083 | (2018.01) |
| G21K 1/10 | (2006.01) |

(52) U.S. Cl.
CPC ............. *H05G 1/30* (2013.01); *G01N 23/083* (2013.01); *G01V 5/0041* (2013.01); *G21K 1/043* (2013.01);
(Continued)

(58) Field of Classification Search
CPC .. H05G 1/30; G01N 23/083; G01N 2223/313; G01N 2223/423;
(Continued)

(56) References Cited

U.S. PATENT DOCUMENTS 5,044,002 A  *  8/1991  Stein ..................... A61B 6/482
                                                              378/158
2007/0104320 A1    5/2007  Arenson et al.
(Continued)

FOREIGN PATENT DOCUMENTS

| CN | 103185734 A | 7/2013 |
| CN | 103431871 A | 12/2013 |

(Continued)

OTHER PUBLICATIONS

Rebuffel V et al, "Dual-energy X-ray imaging: Benefits and limits", Insight—Non-Destructive Testing and Condition Monitoring. British Institute of Non-Destructive Testing, GB, vol. 49, No. 10, Oct. 1, 2007, 12 pages.

(Continued)

*Primary Examiner* — Courtney D Thomas
(74) *Attorney, Agent, or Firm* — Kilpatrick Townsend & Stockton LLP (57) ABSTRACT

Provided is a dual-energy ray scanning system, which includes a ray source for alternately emitting a high energy ray and a low energy ray; a filter includes a low energy filtering element and a low energy transmitting element; a control device for synchronously controlling the ray source and the filter, and the low energy filtering element includes a plurality of filter sheets, the low energy transmitting element comprises a plurality of transmission sheets, the filter sheets and the transmission sheets are arranged alternately and surround the ray source to form a cavity, and the ray source is located on a central axis of the cavity.

13 Claims, 6 Drawing Sheets

(52) U.S. Cl.
CPC ......... *G21K 1/10* (2013.01); *G01N 2223/313* (2013.01); *G01N 2223/423* (2013.01)

(58) Field of Classification Search
CPC ............. G01N 2223/206; G01N 23/04; G01N 23/087; G01V 5/0041; G21K 1/043; G21K 1/10; G06T 11/003; G06T 11/008; G06T 7/002; G06T 2207/30112; G06T 2211/408; G06T 2207/10081
USPC ............................................ 378/57, 155–160
See application file for complete search history.

(56) References Cited

U.S. PATENT DOCUMENTS

| | | |
|---|---|---|
| 2009/0207966 A1 | 8/2009 | Kumat et al. |
| 2012/0163530 A1* | 6/2012 | Sainath ................ A61B 6/027 378/5 |
| 2012/0314834 A1 | 12/2012 | Yao et al. |

FOREIGN PATENT DOCUMENTS

| | | |
|---|---|---|
| CN | 104464871 A | 3/2015 |
| CN | 104535592 A | 4/2015 |
| CN | 105181723 A | 12/2015 |
| EP | 1452890 A2 | 9/2004 |

OTHER PUBLICATIONS

Primak A et al: "Improved dual-energy material discrimination for dual-source CT by means of additional spectral filtration", Medical Physics, AIP, Melville, NY, US, vol. 36. No. 4, Mar. 25, 2009, 11 pages.

International Search Report dated Sep. 28, 2015 for International Patent Application No. PCT/CN2016/099685; all pages. [Note: No English translation available].

* cited by examiner

DUAL-ENERGY RAY SCANNING SYSTEM, SCANNING METHOD AND INSPECTING SYSTEM

FIELD OF THE INVENTION

The present invention relates to the radiation scanning, imaging and detecting field, and particularly relates to a dual-energy ray scanning system, scanning method and inspecting system.

BACKGROUND OF THE INVENTION

In the non-invasive inspection field, X-ray is an important transmission inspection means. For example, after performing X-ray radiation imaging on a vehicle, a prohibited item in the vehicle can be inspected by reviewing and analyzing X-ray scan images, to thereby reach the objective of security inspection.

At present, the X-ray use in transmission inspection has been upgraded from a single energy ray to a high and low dual-energy ray, and the recognition of an object to be inspected is advanced by leaps and bounds based on a difference in penetration characteristics of dual-energy ray.

The main technical indexes for the current security inspection apparatus comprise transmissivity and spatial wire resolution of X-ray. The so-called spatial wire resolution is a degree to which a detector can recognize an iron wire (the diameter of the iron wire is for example 1 mm or 2 mm or etc.) in a space, when the X-ray is irradiated into the iron wire. High energy photons are favorable to the index of transmissivity, because the high energy photons can improve the penetration capability of the ray, but the high energy photons are very unfavorable to the spatial wire resolution, because the high energy photons lost a great amount of information of the object to be inspected. Low energy ray has a better spatial wire resolution, and the low energy ray can image by irradiating the spatial wires.

The energy spectrum of the X-ray is a continuous spectrum, and a low energy portion of its high energy ray influences the transmissivity of the high energy ray. By adding a filter for absorbing low energy photons in a beam exit direction of the ray source, the transmissivity of the high energy ray can be improved, but the spatial wire resolution of the low energy ray will be reduced at the same time. Thus, a problem to be solved in the dual-energy X-ray inspection technology is how to guarantee the index of transmissivity and the index of spatial wire resolution at the same time.

SUMMARY OF THE INVENTION

A technical problem to be solved by the invention is how to guarantee the index of transmissivity and the index of spatial wire resolution at the same time in the dual-energy X-ray inspection technology.

According to a first aspect of the invention, a dual-energy ray scanning system comprises:

a ray source for alternately emitting a high energy ray and a low energy ray;

a filter comprising a low energy filtering element and a low energy transmitting element; and a control device for controlling said ray source and said filter to make said low energy filtering element of said filter be aligned with a beam exit direction of said ray source when said ray source emits a high energy ray so as to filter low energy portion of said high energy ray out and transmit high energy portion of said high energy ray out, and for controlling said ray source and said filter to make said low energy transmitting element of said filter be aligned with said beam exit direction of said ray source when said ray source emits the low energy ray so as to transmit said low energy ray out.

In an embodiment, said low energy filtering element comprises a plurality of filter sheets; said low energy transmitting element comprises a plurality of transmission sheets; said filter sheets and said transmission sheets are arranged alternately and surround said ray source to form a cavity; and said ray source is located on a central axis of said cavity.

In an embodiment, said filter is a hollow cylinder shape and said filter sheets and said transmission sheets are arranged parallel to said central axis of said cavity.

In an embodiment, said filter is of a disc shape, and said low energy filtering element comprises a plurality of filter sheets arranged in a radial direction from a center of said disc, said low energy transmitting element comprises a plurality of transmission sheets, said filter sheets and transmission sheets are arranged alternately and said filter is spatially perpendicular to the beam exit direction of said ray source.

In an embodiment, said filter sheets are equally sized and are arranged with equal distance each other.

In an embodiment, said low energy filtering element is made of a high Z material, and said low energy transmitting element is a void or made of a low Z material, wherein Z represents an atomic number.

In an embodiment, said ray source is an accelerator comprising a target and an electron gun for alternately emitting a high energy electron beam or a low energy electron beam, wherein said high energy electron beam bombards said target to generate a high energy ray and said low energy electron beam bombards said target to generate a low energy ray.

In an embodiment, said ray source is an accelerator comprising an electron gun for emitting an electron beam and a target comprising a first part made of a first material and a second part made of a second material, wherein said electron beam emitted by said electron gun alternately bombard said first part or said second part of said target to respectively generate a high energy ray or a low energy ray.

According to a second aspect of the invention, a dual-energy ray inspecting system comprises the foregoing-mentioned dual-energy ray scanning system.

In an embodiment, said dual-energy ray inspecting system is a fix-mounted type dual-energy ray inspecting system, a movable type dual-energy ray inspecting system, or a vehicle-mounted type dual-energy ray inspecting system.

According to a third aspect of the invention, a dual-energy ray scanning method comprises: alternately emitting a high energy ray and a low energy ray by a ray source; and controlling said ray source and said filter to make a low energy filtering element of a filter be aligned with a beam exit direction of said ray source when said ray source emits a high energy ray so as to filter low energy portion of said high energy ray out and transmit high energy portion of said high energy ray out, and to make a low energy transmitting element of said filter be aligned with said beam exit direction of said ray source when said ray source emits a low energy ray so as to transmit said low energy ray out.

In an embodiment, said low energy filtering element is made of a high Z material, said low energy transmitting element is a void or made of a low Z material, wherein Z represents an atomic number.

According to a forth aspect of the invention, a computer readable storage medium is provided. The computer readable storage medium stores a computer program and said program is executed by a processor to implement said a dual-energy ray scanning method.

According to a fifth aspect of the invention, a computer device is provided. The computer device comprises a memory, a processor, and a computer program which is stored in said memory and can be run by said processor; said processor executes said a dual-energy ray scanning method by running said program.

In the invention, when the ray source emits the high energy ray, the low energy filtering element of the filter can filter out the low energy portion of the high energy ray, and when the ray source emits the low energy ray, the low energy transmitting element of the filter can transmit out the low energy ray, which not only can improve transmissivity of the high energy ray, but also does not lose the spatial wire resolution of the low energy ray, and which guarantees the index of transmissivity and the index of spatial wire resolution at the same time, such that the dual-energy ray can sufficiently utilize a difference in its penetration characteristics to recognize the object to be inspected, thereby reaching the objective of security inspection.

BRIEF DESCRIPTION OF THE DRAWINGS

In order to describe more clearly the embodiments of the invention or the technical solutions in the prior art, the drawings to be used for describing the embodiments or the prior art are briefly discussed as below. But it is obvious that the drawings described below merely are directed to some embodiments of the invention, and those skilled in the art could obtain other drawings from the accompanying drawings without any inventive efforts.

DETAILED DESCRIPTION OF THE EMBODIMENTS

The preferred embodiments of the invention will be described in more detail below with reference to the drawings. Although the drawings show preferred embodiments the invention, it should be appreciated that, the invention can be carried out in various forms and should not be limited by the embodiments set forth here.

Figure 1A:
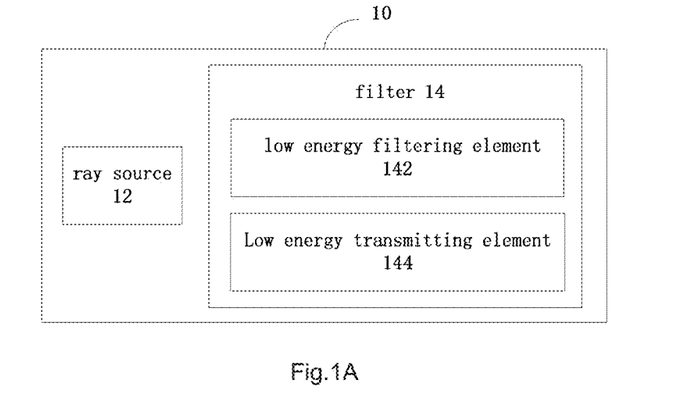
FIG. 1A is a schematic diagram showing a structure of an embodiment according to the dual-energy X-ray scanning system of the invention.
Figure 1B:
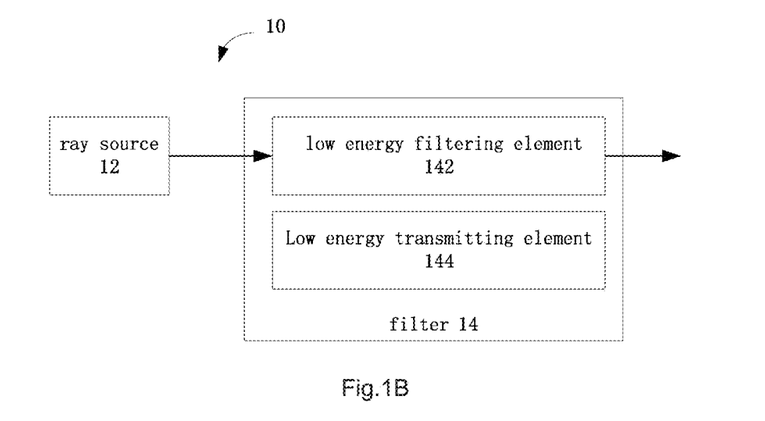
FIG. 1B is a schematic diagram showing a high energy ray filtering principle of the system shown in FIG. 1A.
Figure 1C:
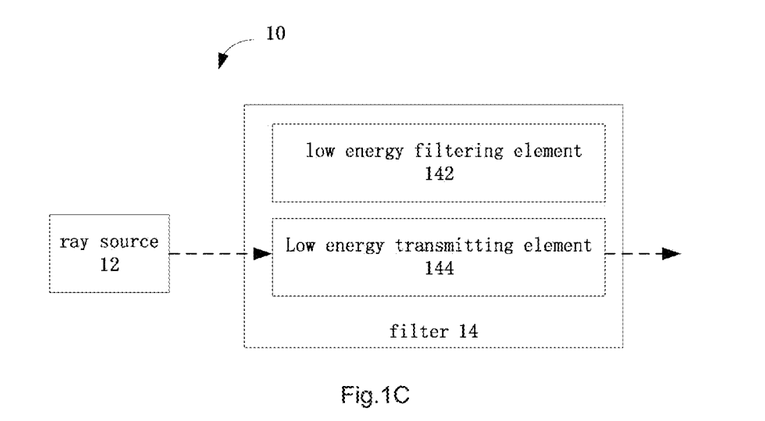
FIG. 1C is a schematic diagram showing a low energy ray filtering principle of the system shown in FIG. 1A.

Refer to the schematic diagram of the dual-energy X-ray scanning system shown in FIG. 1A. The dual-energy ray scanning system 10 according to the invention comprises a ray source 12 and a filter 14, wherein the ray source 12 is used for emitting two kinds of rays, namely, a high energy ray and a low energy ray, and in general, the ray source 12 can alternately emit the high energy ray and the low energy ray. The filter 14 is used for filtering the high energy ray and the low energy ray emitted by the ray source. The filter 14 comprises a low energy filtering element 142 and a low energy transmitting element 144. By referring to the schematic diagram of the high energy ray filtering principle shown in FIG. 1B, wherein the solid lines represent the high energy ray and the arrow direction represents the exit direction of the ray, when the ray source 12 emits the high energy ray, the low energy filtering element 142 of the filter 14 is aligned with a beam exit direction of the ray source 12, such that the low energy portion of the high energy ray is filtered out by the low energy filtering element 142, and the high energy portion of the high energy ray is transmitted out from the low energy filtering element 142. By referring to the schematic diagram of the low energy ray filtering principle shown in FIG. 1C, wherein the dotted lines represents the low energy ray and the arrow direction represents the exit direction of the ray, when the ray source 12 emits the low energy ray, the low energy transmitting element 144 of the filter 14 is aligned with the beam exit direction of the ray source 12, such that the low energy ray is transmitted out from the low energy transmitting element 144. This not only can improve transmissivity of the high energy ray, but also does not lose the spatial wire resolution of the low energy ray, and this guarantees the index of transmissivity and the index of spatial wire resolution at the same time, such that the dual-energy ray can sufficiently utilize a difference in its penetration characteristics to recognize the object to be inspected, wherein the high energy imaging can be used for checking the index of transmissivity and the low energy imaging can be used for checking the index of spatial wire resolution, thereby reaching the objective of security inspection.

By changing the type and thickness of the materials of the low energy filtering element 142 and the low energy transmitting element 144, different filtering functions can be achieved.

The high energy ray is relative to the low energy ray. By taking the X-ray as an example, the first case, the X-ray lower than 1 MeV is the low energy ray while the X-ray greater than 1 MeV is the high energy ray. The second case, in the high energy dual-energy X-ray scanning system, both the low energy ray and the high energy ray are greater than 1 MeV, and the X-ray about 3 MeV is the low energy ray while the X-ray about 6 MeV or higher is the high energy ray.

Preferably, the ray source 12 for example may be a device capable of generating a dual-energy X-ray. The ray source of the dual-energy X ray for example may be implemented by using an accelerator, and two illustrative dual-energy ray generation modes are listed below. The first one, the accelerator comprises an electron gun and a target made of one material, wherein the electron gun alternately emits a high energy electron beam and low energy electron beam, wherein the high energy electron beam bombards the target to generate high energy rays, and the low energy electron beam bombards the target to generate low energy rays. The second one, the accelerator comprises an electron gun and a target made of two materials, i.e., the target is divided into two parts and the two parts are made of different type of material respectively, and the electron beams emitted by the electron gun alternately bombard the two parts of the target to respectively generate high energy rays and low energy rays. The target material generally comprises W, Mo, Au, Cu, and etc. Since different materials have different characteristic spectrum, the X-ray generated by a different target material under the same anode voltage has different characteristic peaks, i.e., an X-ray with a different energy. Furthermore, the accelerator may be any device capable of accelerating the charged particles such as a cyclotron, a linear accelerator, an electrostatic accelerator, a particle accelerator, a multivoltage accelerator, and a low cost electron inductive accelerator.

The ray source 12 may also be a device that generates other dual-energy radiation radiographic rays, e.g., a ray source of dual-energy gamma rays, a ray source of a dual-energy neutron rays, and the like.

The filter 14 has various kinds of implementations. For example, the filter 14 is implemented by using a hollow 3D structure, the low energy filtering element 142 and the low energy transmitting element 144 are provided on an outer surface of the 3D structure, and the ray source 12 is placed in the hollow portion of the 3D structure. Again for example, the filter 14 is implemented by using a planar structure, the low energy filtering element 142 and the low energy transmitting element 144 are provided on the planar structure, and the planar structure is placed spatially perpendicular to the beam exit direction of the ray source 12. Some illustrative preferred implementations are listed below.

A preferred implementation of the filter 14 of the 3D structure is that, a surface of the filter 14 forms a cavity, and filter sheets arranged in strips for example serving as the low energy filtering element 142 are provided on the surface of the filter 14, separation portions (i.e. transmission sheets) between the filter sheets serve as the low energy transmitting element 144, and the ray source 12 is located on a central axis of the filter 14 within the cavity.

Figure 2A:
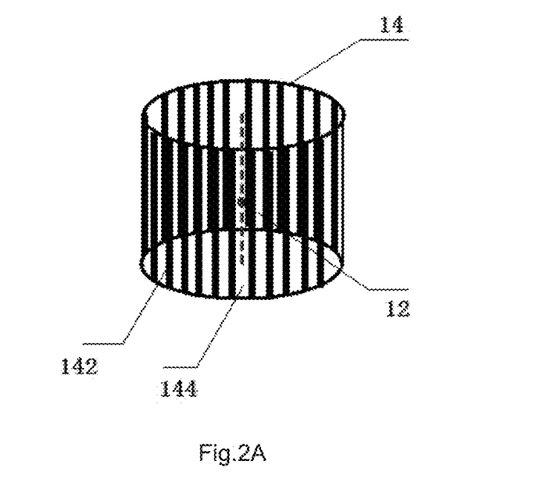
FIGS. 2A and 2B are a stereogram and a top view of the dual-energy X-ray scanning system of the invention in which the filter is of a hollow cylinder shape.
Figure 2B:
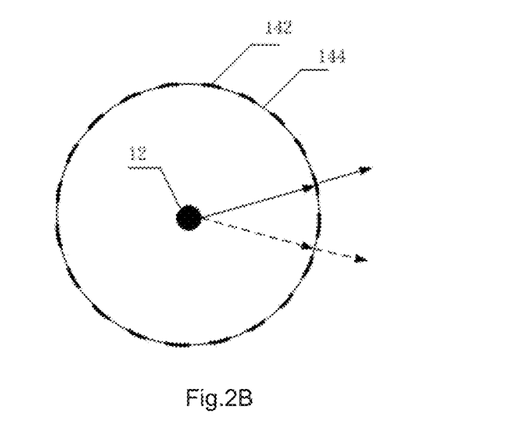

FIGS. 2A and 2B are a stereogram and a top view of the dual-energy X-ray scanning system of the invention in which the filter is of a hollow cylinder shape. Preferably, the filter 14 may be a hollow cylinder, and the ray source 12 is located on a central axis of the hollow cylinder, for example, in a body center of the hollow cylinder, and filter sheets arranged in strips are provided in a direction parallel to the central axis on the surface of the hollow cylinder. In order to facilitate synchronous control of the ray source 12 with the filter 14, preferably, the filter sheets may be equally sized and equally distanced from each other. At this time, by making the rotation frequency of the hollow cylinder the same with the beam-exiting frequency of the high and low energy rays, the synchronous control can be achieved. In the implementation of the hollow cylinder, the lengths from the ray source 12 to the various filter sheets and their gap portions are equal for the convenience of synchronous control, and with reference to FIG. 2B, wherein the high energy ray is represented by solid lines, and the low energy ray is represented by dotted lines, the arrow direction represents the ray direction, the beam exit direction of the ray source 12 is perpendicular to the filter sheets and their gap portions, thereby obtaining a better filtering effect.

Besides, the filter 14 may adopt a hollow spindle structure, a hollow ellipsoid structure, a hollow truncated cone structure and etc., and preferably, the ray source 12 is located in a body center of these hollow structures. By making the rotation frequency of these hollow structures the same with the beam-exiting frequency of the high and low energy rays, the synchronous control can be achieved.

Further, the filter 14 can be implemented by adopting some other alternative structures. For example, the filter 14 may be a hollow cuboid, and the ray source 12 is located in a central axis of the hollow cuboid, and the filter sheets are provided in a direction in parallel to the central axis on the surface of the hollow cuboid. In the implementations of the hollow cuboid, the lengths from the ray source 12 to the filter sheets and to their gap portions are somewhat different, the rotational angle of the filter 14 should be adjusted in real time to perform alignment, and the synchronous control is relatively comparatively complex.

Figure 3A:
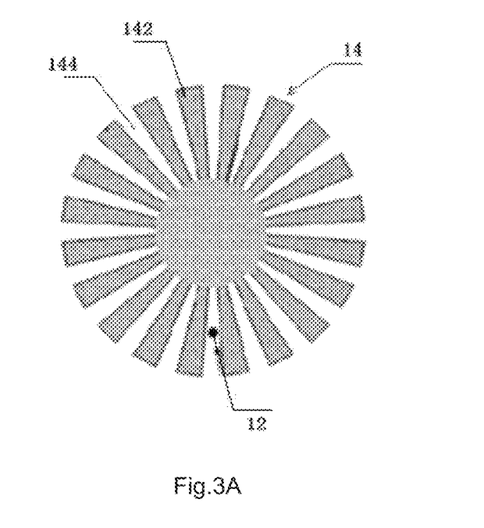
FIGS. 3A and 3B are a side view and a stereogram of the dual-energy X-ray scanning system of the invention in which the filter is of a disc shape.
Figure 3B:
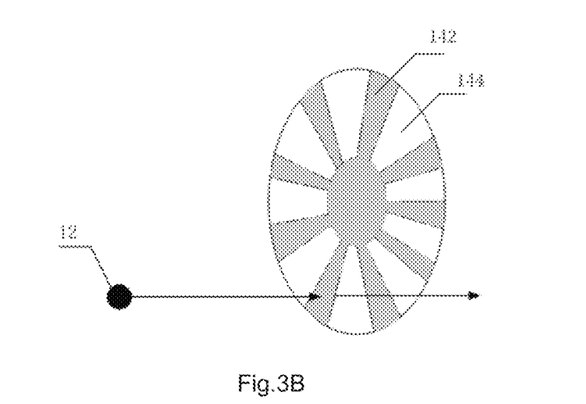

FIGS. 3A and 3B are a side view and a stereogram of the dual-energy ray scanning system of the invention in which the filter is of a disc shape. A preferable implementation of the filter 14 of a planar structure is that, the filter 14 is of a disc shape, the filter sheets serving as the low energy filtering element 142 is arranged to radiate outwards in a radial direction from the center of the disc, and the separation portions between the filter sheets serve as the low energy transmitting element 144 (the separation portions may also be regarded as transmission sheets). By referring to FIG. 3B, the disc is spatially perpendicular to the beam exit direction of the ray source 12, and the ray source 12 is located in a filter sheet region of the disc. In order to facilitate the synchronous control of the ray source 12 with the filter 14, preferably, the filter sheets may be equally sized and equally distanced from each other.

In a specific implementation of the filter 14, the filter 14 can be coupled to a shaft, and can rotate about the shaft. In the synchronous control, the current position information of the filter 14 is detected, and the ray source 12 is controlled to emit rays with a corresponding energy; if the low energy filtering element 142 of the current filter 14 is aligned with the beam exit direction of the ray source 12, then the ray source 12 is controlled to emit high energy rays, and if the low energy transmitting element 144 of the current filter 14 is aligned with the beam exit direction of the ray source 12, then the ray source 12 is controlled to emit low energy rays, subsequently, by cooperatively controlling the rotation frequency of the filter 14 and the beam-exiting frequency of the high and low energy rays of the ray source 12, such that, when the ray source emits high energy rays, the low energy filtering element of the filter is aligned with the beam exit direction of the ray source, and when the ray source emits low energy rays, the low energy transmitting element of the filter is aligned with the beam exit direction of the ray source, that is, the synchronous control of the ray source 12 with the filter 14 can be achieved.

Figure 4A:
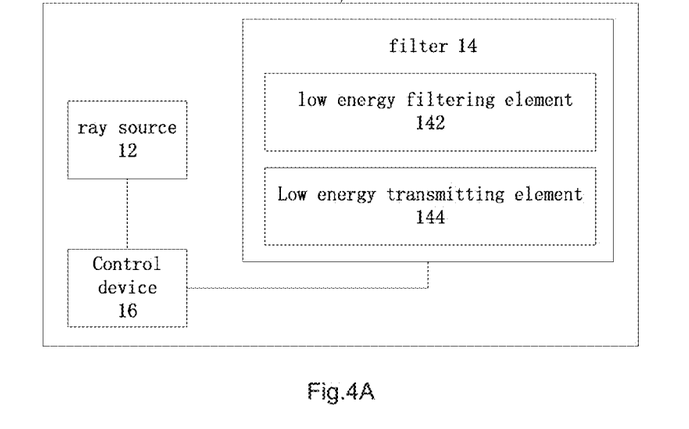
FIG. 4A is a schematic diagram showing a structure of an embodiment of the dual-energy X-ray scanning system of the invention comprising a control device.
Figure 4B:
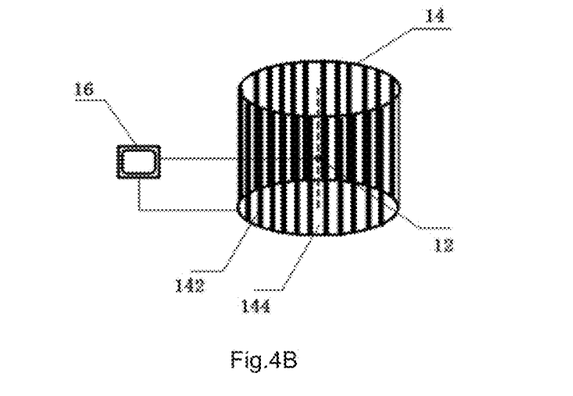
FIG. 4B is a principle schematic diagram showing that the control device of the invention synchronously controls the ray source and the filter of a hollow cylinder shape.
Figure 4C:
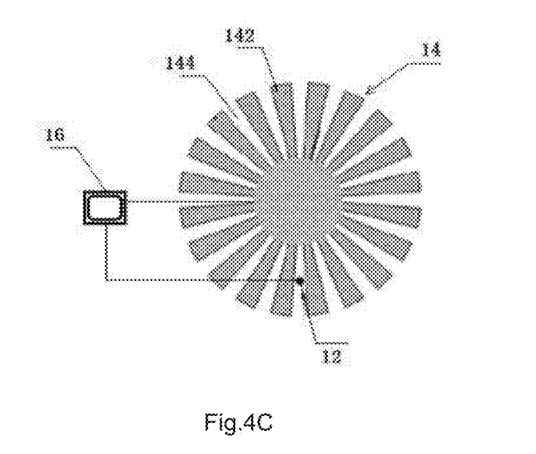
FIG. 4C is a principle schematic diagram showing that the control device of the invention synchronously controls the ray source and the filter of a disc shape.

Regarding the synchronous control of the ray source 12 with the filter 14, the first manner (i.e. an active-synchro manner) is as follows: respectively setting the beam-exiting frequency of the high and low energy rays of the ray source 12 and the rotation frequency of the filter 14 such that the two remain cooperatively consistent, that is, when the ray source emits high energy rays, the low energy filtering element of the filter is aligned with the beam exit direction of the ray source, and when the ray source emits low energy rays, the low energy transmitting element of the filter is aligned with the beam exit direction of the ray source, thereby achieving the synchronous control between the two; such a synchronous control is comparatively simple, readily achievable, but is not intelligent enough and should be set in advance. Thus, the following second manner (i.e. a passive-synchro manner) may be adopted: a control device 16 is added to the dual-energy ray scanning system 10; by referring to FIG. 4A, the control device 16 controls the ray source 12 and the filter 14 synchronously, such that when the ray source 12 emits high energy rays, the low energy filtering element of the filter 14 is aligned with the beam exit direction of the ray source 12, the low energy portion of the high energy rays is filtered out by the low energy filtering element 142 and the high energy portion of the high energy rays is transmitted out from the low energy filtering element 142, and when the ray source 12 emits low energy rays, the low energy transmitting element of the filter 14 is aligned with the beam exit direction of the ray source 12 and the low energy rays are transmitted out from the low energy transmitting element 144; such a synchronous control is more intelligent and flexible. FIG. 4B is a principle schematic diagram showing that the control device 16 synchronously controls the ray source 12 and the filter 14 of a hollow cylinder shape. FIG. 4C is a principle schematic diagram showing that the control device 16 synchronously controls the ray source 12 and the filter 14 of a disc shape.

The low energy filtering element 142 involved in the above embodiments can be formed of a high Z material, wherein Z represents an atomic number, and the high Z material may cause the low energy portion of the high energy rays to be filtered out and the high energy portion of the high energy rays to be transmitted out. The high Z material for example may comprise at least one of W, Pb, U, and etc. A suitable high Z material can be selected according to filtering needs of the low energy portion. The low energy transmitting element 144 may be a void through which the low energy rays can be directly transmitting out, or may be formed of a low Z material. The low Z material may comprise at least one of graphite, boron, polythene, or other hydrogen-rich organic materials. A suitable low Z material or void structure can be selected according to transmitting needs of the low energy portion.

Figure 5:
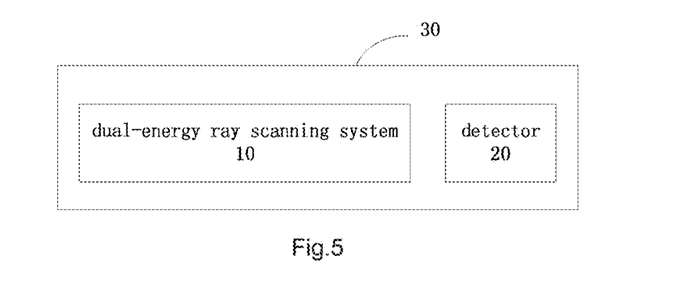
FIG. 5 is a schematic diagram showing a structure of an embodiment of the dual-energy X-ray inspecting system of the invention.

The dual-energy ray scanning system 10 of the invention may be applied to a dual-energy ray inspecting system, wherein the dual-energy ray inspecting system may be for example a fix-mounted type dual-energy ray inspecting system, a movable type dual-energy ray inspecting system, or a vehicle-mounted type dual-energy ray inspecting system, but is not limited to the above examples listed. As shown in FIG. 5, the dual-energy ray inspecting system 30 comprises, in addition to the dual-energy ray scanning system 10, a detector 20 for detecting rays after transmitting the object to be inspected. The detector 20 may be a dual-energy detector group, that is, it not only comprises low energy detectors sensitive to the low energy rays but also comprise high energy detectors sensitive to the high energy rays at each position point. Once the ray source generates a ray, the dual-energy detector group can obtain a high energy image and a low energy image at the same time, which can obtain more information and improve a finally detected image quality of the product to be detected. Furthermore, the dual-energy ray inspecting system may further comprise devices such as collimator, image display and so on.

Figure 6:
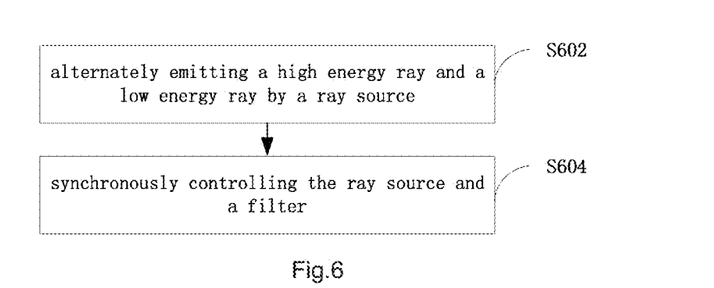
FIG. 6 is a schematic diagram showing a flowchart of an embodiment of the dual-energy X-ray scanning method of the invention.

By referring to the flowchart shown in FIG. 6, a dual-energy ray scanning method provided by the invention comprises the steps of:

S602: alternately emitting a high energy ray and a low energy ray by a ray source 12; and S604: synchronously controlling the ray source 12 and a filter 14, such that the filter 14 filters out a low energy portion of the high energy ray when the ray source 12 emits the high energy ray, and the filter 14 transmits out the low energy ray when the ray source 12 emits the low energy ray.

The filter 14 comprises a low energy filtering element 142 and a low energy transmitting element 144, wherein the synchronously controlling step S604 specifically comprises: when the ray source 12 emits the high energy ray, the low energy filtering element of the filter 14 is aligned with a beam exit direction of the ray source 12, such that the low energy portion of the high energy ray is filtered out by the low energy filtering element 142 and the high energy portion of the high energy ray is transmitted out from the low energy filtering element 142, and when the ray source 12 emits the low energy ray, the low energy transmitting element 144 of the filter 14 is aligned with the beam exit direction of the ray source 12, such that the low energy ray is transmitted out from the low energy transmitting element 144. This not only can improve transmissivity of the high energy ray, but also does not lose the spatial wire resolution of the low energy ray, and this guarantees the index of transmissivity and the index of spatial wire resolution at the same time, such that the dual-energy ray can sufficiently utilize a difference in its penetration characteristics to recognize the object to be inspected, wherein the high energy imaging can be used for checking the index of transmissivity and the low energy imaging can be used for checking the index of spatial wire resolution, thereby reaching the objective of security inspection.

Figure 7:
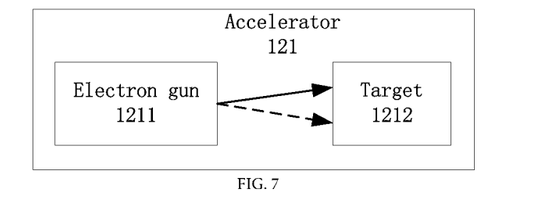
FIG. 7 is a schematic diagram showing a schematic diagram of dual-energy ray generation modes of the invention.

Turning now to FIG. 7 which describes an accelerator 121 which includes an electron gun 1211 which is in communication with a target 1212. In one embodiment, electron gun 1211 alternately emits a high energy electron beam or a low energy electron beam, and the high energy electron beam bombards target 1212 to generate a high energy ray and the low energy electron beam bombards target 1212 to generate a low energy ray.

Figure 8:
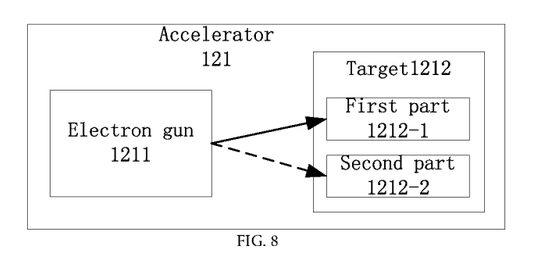
FIG. 8 is a schematic diagram showing a schematic diagram of dual-energy ray generation modes of the invention.

Turning now to FIG. 8 which further describes accelerator 121. In FIG. 8 target 1212 includes a first part 1212-1 and a second part 1212-2. In one embodiment, first part 1212-1 is made of a first material and second part 1212-2 is made of a second material. The electron beam emitted by electron gun 1211 alternately bombards first part 1212-1 or second part 1212-2 of target 1212 to respectively generate a high energy ray or a low energy ray.

A computer readable storage medium which stores a computer program, the program is executed by a processor to implement the following steps: controlling a ray source and a filter to make a low energy filtering element of the filter be aligned with a beam exit direction of the ray source when the ray source emits a high energy ray so as to filter low energy portion of the high energy ray out and transmit high energy portion of the high energy ray out, and to make a low energy transmitting element of the filter be aligned with the beam exit direction of the ray source when the ray source emits a low energy ray so as to transmit the low energy ray out.

A computer device which comprises a memory, a processor, and a computer program which is stored in the memory and can be run by the processor, the processor executes the following steps by running the program: controlling a ray source and a filter to make a low energy filtering element of the filter be aligned with a beam exit direction of the ray source when the ray source emits a high energy ray so as to filter low energy portion of the high energy ray out and transmit high energy portion of the high energy ray out, and to make a low energy transmitting element of the filter be aligned with the beam exit direction of the ray source when the ray source emits a low energy ray so as to transmit the low energy ray out.

Furthermore, the method according to the invention may be also implemented as a computer program product comprising a computer readable medium on which a computer program for performing the functions defined in the method of the invention is stored. The skilled in the art would appreciate that, the various illustrative logical blocks, modules, circuits and algorithm steps could be implemented as an electronic hardware, computer software or a combination thereof.

The skilled in the art may change the specific implementations and application ranges according to the concept in the embodiments of the present invention. In view of the above, the specification shall not be construed as a limit to the present invention.

The invention claimed is:

1. A dual-energy ray scanning system, characterized in that said system comprises:
   a ray source for alternately emitting a high energy ray and a low energy ray;
   a filter comprising a low energy filtering element and a low energy transmitting element; and
   a control device for controlling said ray source and said filter to make said low energy filtering element of said filter be aligned with a beam exit direction of said ray source when said ray source emits a high energy ray so as to filter low energy portion of said high energy ray out and transmit high energy portion of said high energy ray out, and for controlling said ray source and said filter to make said low energy transmitting element of said filter be aligned with said beam exit direction of said ray source when said ray source emits the low energy ray so as to transmit said low energy ray out;
   wherein said low energy filtering element comprises a plurality of filter sheets;
   said low energy transmitting element comprises a plurality of transmission sheets;
   said filter sheets and said transmission sheets are arranged alternately and surround said ray source to form a cavity; and
   said ray source is located on a central axis of said cavity.

2. The dual-energy ray scanning system according to claim 1, characterized in that:
   said filter is a hollow cylinder shape; and
   said filter sheets and said transmission sheets are arranged parallel to said central axis of said cavity.

3. The dual-energy ray scanning system according to claim 1, characterized in that said filter sheets are equally sized and are arranged with equal distance each other.

4. The dual-energy ray scanning system according to claim 2, characterized in that said filter sheets are equally sized and are arranged with equal distance each other.

5. The dual-energy ray scanning system according to claim 1, characterized in that:
   said low energy filtering element is made of a high Z material; and
   said low energy transmitting element is a void or made of a low Z material,
   wherein Z represents an atomic number.

6. The dual-energy ray scanning system according to claim 1, characterized in that said ray source is an accelerator comprising a target and an electron gun for alternately emitting a high energy electron beam or a low energy electron beam, wherein said high energy electron beam bombards said target to generate a high energy ray and said low energy electron beam bombards said target to generate a low energy ray.

7. The dual-energy ray scanning system according to claim 1, characterized in that said ray source is an accelerator comprising an electron gun for emitting an electron beam and a target comprising a first part made of a first material and a second part made of a second material, wherein said electron beam emitted by said electron gun alternately bombard said first part or said second part of said target to respectively generate a high energy ray or a low energy ray.

8. A dual-energy ray inspecting system, characterized in that said dual-energy ray inspecting system comprises a dual-energy ray scanning system according to claim 1.

9. The dual-energy ray inspecting system according to claim 8, characterized in that said dual-energy ray inspecting system is a fix-mounted type dual-energy ray inspecting system, a movable type dual-energy ray inspecting system, or a vehicle-mounted type dual-energy ray inspecting system.

10. A dual-energy ray scanning method, characterized in that said method comprises:
    alternately arranging a plurality of filter sheets of a low energy filtering element of a filter and a plurality of transmission sheets of a low energy transmitting element of the filter to form a cavity;
    alternately emitting a high energy ray and a low energy ray by a ray source located on a central axis of the cavity; and
    controlling said ray source and a filter to make a low energy filtering element of said filter be aligned with a beam exit direction of said ray source when said ray source emits a high energy ray so as to filter low energy portion of said high energy ray out and transmit high energy portion of said high energy ray out, and to make a low energy transmitting element of said filter be aligned with said beam exit direction of said ray source when said ray source emits a low energy ray so as to transmit said low energy ray out.

11. The dual-energy ray scanning method according to claim 10, characterized in that said low energy filtering element is made of a high Z material, said low energy transmitting element is a void or made of a low Z material, wherein Z represents an atomic number.

12. A computer readable storage medium which stores a computer program, characterized in that said program is executed by a processor to implement said a dual-energy ray scanning method according to claim 10.

13. A computer device which comprises a memory, a processor, and a computer program which is stored in said memory and can be run by said processor, said computer device is characterized in that said processor executed said a dual-energy ray scanning method according to claim 10 by running said program.

* * * * *